United States Patent [19]

Hren et al.

[11] 4,202,337
[45] May 13, 1980

[54] BIPOLAR ELECTROSURGICAL KNIFE

[75] Inventors: John J. Hren; David E. Clark; David A. Jenkins; Paul F. Johnson, III, all of Gainesville; Howead E. Degler, Jr., St. Petersburg, all of Fla.

[73] Assignee: Concept, Inc., Clearwater, Fla.

[21] Appl. No.: 806,529

[22] Filed: Jun. 14, 1977

Related U.S. Application Data

[63] Continuation-in-part of Ser. No. 695,649, Jun. 14, 1976, abandoned.

[51] Int. Cl.² .................. A61B 17/36; A61N 3/02
[52] U.S. Cl. .................. 128/303.14; 128/303.17
[58] Field of Search .................. 128/303.13–303.18, 128/405, 800

[56] References Cited

U.S. PATENT DOCUMENTS

| | | | |
|---|---|---|---|
| 1,735,271 | 11/1929 | Groff | 128/303.14 |
| 1,814,791 | 7/1931 | Ende | 128/303.17 |
| 3,163,165 | 12/1964 | Isikawa | 128/303.17 |
| 3,532,095 | 10/1970 | Miller et al. | 128/303.13 |
| 3,685,518 | 8/1972 | Beuerle | 128/303.17 |
| 3,699,967 | 10/1972 | Anderson | 128/303.14 |
| 3,768,482 | 10/1973 | Shaw | 128/303.14 |
| 3,901,242 | 8/1975 | Storz | 128/303.15 |
| 3,920,021 | 11/1975 | Hiltebrandt | 128/303.17 |
| 3,987,795 | 10/1976 | Morrison | 128/303.14 |
| 4,014,343 | 3/1977 | Esty | 128/303.14 |

FOREIGN PATENT DOCUMENTS

| | | | |
|---|---|---|---|
| 564168 | 10/1958 | Canada | 128/303.14 |
| 2428886 | 1/1976 | Fed. Rep. of Germany | 128/303.14 |
| 2268505 | 11/1975 | France | 128/303.14 |
| 243478 | 7/1946 | Switzerland | 128/303.18 |

*Primary Examiner*—Lee S. Cohen
*Attorney, Agent, or Firm*—Gipple & Hale

[57] ABSTRACT

An electrosurgical instrument for cutting, spot coagulation and point coagulation comprising a nonconductive handle which holds a blade assembly comprising a plurality of electrodes and an insulation member separating the electrodes.

The blade assembly comprises an active center electrode of specified thickness with a recessed tip and is mounted to an extruded insulation member so that it extends outwardly from the insulation member to form a cutting edge.

Split side return electrodes are symmetrically mounted to the insulation member and separated from the center electrode by the insulation member. The electrode area ratio of the return electrode area to the active electrode area falls between 0.70 and 2.0 allowing consistent bipolar operation.

The electrodes are connected inside the nonconductive handle to a circuit whose output consists of a high frequency electrical current which forms a circuit through tissue intervening between and in contact with the electrodes when the instrument is used.

19 Claims, 15 Drawing Figures

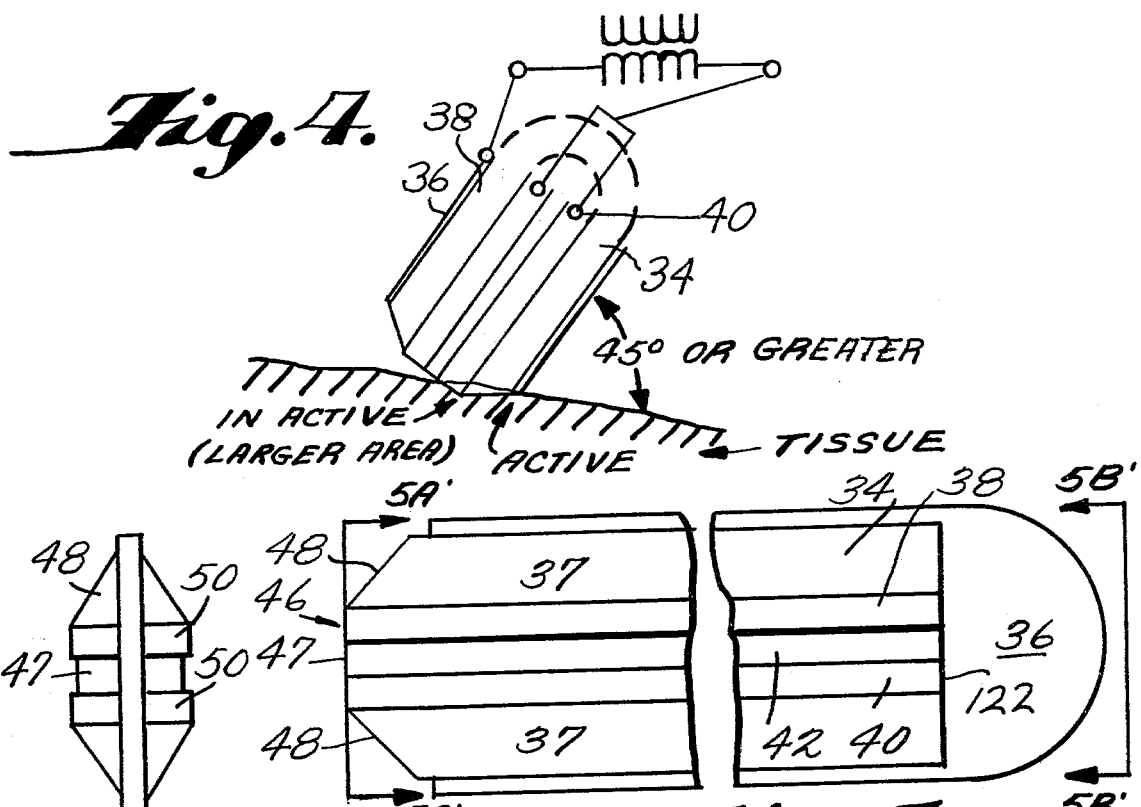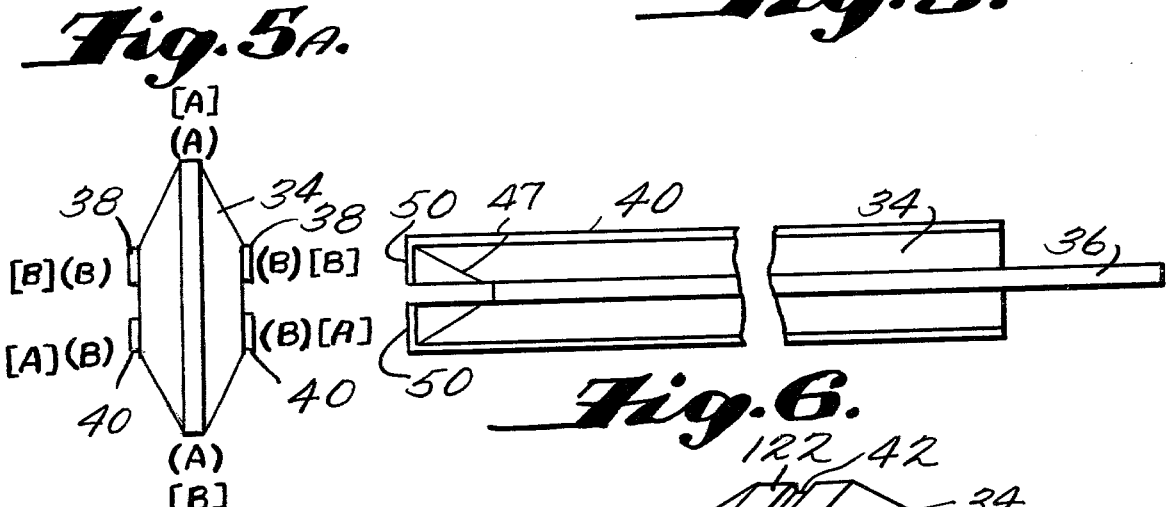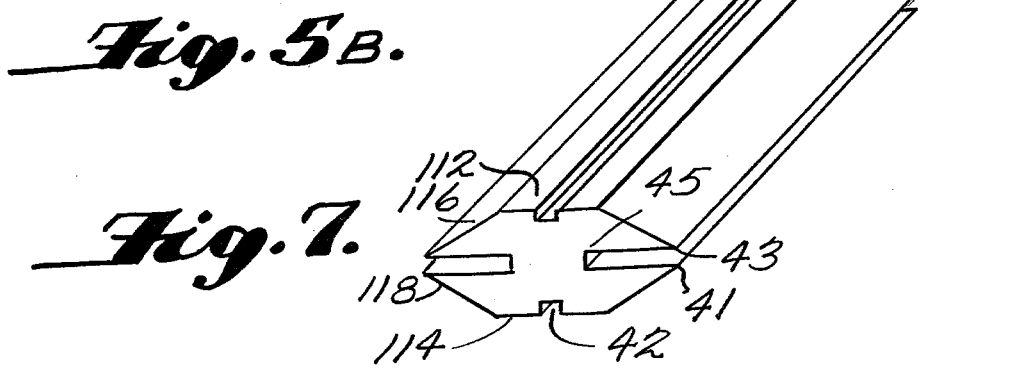

BIPOLAR ELECTROSURGICAL KNIFE

This is a continuation-in-part application of U.S. Patent Application Ser. No. 695,649 filed June 14, 1976 now abandoned.

FIELD OF INVENTION

This invention relates in general to surgical instruments and more particularly to a sterilized bi-polar electrosurgical instrument capable of selectively cutting tissue and/or coagulating materials. Specifically, a novel configuration, composition and construction of the electrosurgical blade tip is described.

DESCRIPTION OF THE PRIOR ART

It is well known in the prior art to use various types of high frequency current in electrical surgical apparatus to perform surgical operations.

In the use of electrosurgical apparatus employing high frequency currents, tissue destruction is produced by a oscillating high frequency electrical field about the electrodes which conducts the oscillating electrical energy in a high concentrated fashion to the tissue. The resistance of the tissue to the oscillations causes mechanical disruption of the cells and heat.

The most commonly used electrical surgical apparatus is of the monopolar type in which an active electrode is used in connection with a metal ground plate on which a patient is positioned.

This type of electrosurgical apparatus falls within the classification of biterminal operation. The return electrode functions to disperse the oscillating current harmlessly over a large area while the treatment electrode concentrates the energy on a smaller point of the tissue. Thus a complete circuit is formed so that various cutting or coagulating procedures can be accomplished. Such an electrical device is shown in U.S. Pat. No. 3,601,126. Electrosurgical units of this type may be hazardous in that they require a ground or return plate to minimize the patient to ground impedance and to complete the radio frequency circuit. Units requiring such a ground plate may not only hinder the operator and present a psychological deterent to a patient but also subject the patient to the possibility of a radio frequency burn when non-uniform contact is made between the ground plate and the patient's skin. Various other electrosurgical instruments utilize a hand held surgical instrument which can be operated from separate power supplies so that the tip of the instrument is provided with either a cutting energization or a coagulating energization. Patents which show the use of such surgical instruments are U.S. Pat. No. 3,875,945 and U.S. Pat. No. 3,699,967.

In U.S. Pat. No. 3,699,967 an electrosurgical generator with a single power stage generates three distinct and independent currents. The three stages comprise coagulation current for hemostasis or tissue destruction, a pure cutting current for cutting with a minimum amount of hemostasis; and a blended cutting current with a moderate amount of hemostasis. The electrosurgical generator includes a solid state power stage driven by two discrete frequencies that provide substantially different cutting and coagulation characteristics. An indicator circuit is provided which is used for providing an audio and visual indication of the electrosurgical generator. Furthermore, the generator provides electrical isolation on all output connections to thereby prevent patient burns caused by alternate return current paths.

Various attempts have been made to develop electrosurgical instruments which do not have a monopolar arrangement or are not provided with hot resistance tips. Such developments have taken the form of bipolar and multipolar surgical instruments. One such bipolar instrument is shown by U.S. Pat. No. 166,184. In this patent an electrode is disclosed with a solid nonconductive head into which electrode wires are imbedded so that they are insulated from each other. Another U.S. Pat. No. 1,814,791 discloses a bipolar coagulating instrument in which electrodes are partially imbedded in the lateral surface of an insulated tip a uniform distance apart so that an output circuit is completed through the tissue intervening between and in contact with the electrodes. A third U.S. Pat. No. 1,983,669 discloses a bipolar coagulating device in which two twisted wires are separated from one another by lamination of an insulative material. A multipolar instrument is shown by U.S. Pat. No. 3,460,539 wherein a surgical instrument is described which has a plurality of exposed conducting rods circumferentially placed in the body of the insulating material for cauterization.

U.S. Pat. Nos. 3,970,088 and 3,987,795 relate to electrosurgical devices utilizing a sesquipolar electrode structure. These devices are used to cut, coagulate and treat human tissue by utilizing a return electrode which is asymmetrically disposed with respect to the conductive element of the active electrode. The surgical devices are constructed so that the active electrode is separated from the tissue when the device is placed in contact with the tissue to insure that a current arc is established between the active electrode and the tissue. In operation of the sesquipolar devices, arc or other large voltage drop processes are active at one electrode only, unlike that of bipolar apparatus. In addition both active and return electrodes are in the operation site as is the case of the bipolar and the device's electrode area ratio between the return electrode area with respect to the active electrode area ranges from 2-200.

Other electrosurgical patents of interest are a Swiss Pat. No. 243,478 which teaches the shorting of side electrodes in a housing having switch means for an energy source; a U.S. Pat. No. 1,735,271 which discloses a diathermy knife with an elongated head provided with a V-shaped cutting edge, a beveled end, a slot having a wide portion and a narrow portion with intervening shoulders; and U.S. Pat. No. 3,901,242. This patent shows an electric surgical instrument which includes a pair of laterally spaced hollow tubes, the distal ends of which are interconnected by a transverse electrical insulating member upon which are helically wound a pair of spaced electrodes having electrical conductors which extend through the tubes for connection to a source of high frequency current. Additional patents of interest are U.S. Pat. Nos. 452,220; 1,916,722; 2,056,377; 2,275,187 and 3,858,586.

The present invention provides a unitary bipolar electrosurgical device that can be used for either cutting or coagulating procedures when used in conjunction with a proper electrosurgical generator. The tissue in the proximal area surrounding the blade is used to close the circuit between the insulated electrodes on the blade.

SUMMARY OF INVENTION

The present invention discloses a disposable hand held electrosurgical cutting and coagulating device in which the type of cutting or coagulating current desired is selected by the setting of a switch which activates the proper circuitry thus transferring the desired mode of current to the novel electrode configuration forming the blade of the surgical instrument. Thus the instrument can perform selected electrosurgical functions without the need of utilizing separate cutting tips or different instruments.

The instrument uses a novel blade assembly comprising an insulation member, a center electrode mounted to the insulation member and symmetrical split side electrodes secured to the insulation member and separated from the center electrode. The blade components form an angled center electrode cutting edge which extends beyond the insulation member. The thickness of the center electrode and extension of the same form an optimum electrode area ratio with the split side electrodes thus decreasing drag force and allowing cleaner incisions.

Performance of the present bipolar blade as compared with a monopolar blade exhibit the following general characteristics: (1) cutting is performed at a much lower power than with a monopolar blade; (2) at identical power settings and cutting speeds, the bipolar blade leaves a cleaner incision than the monopolar blade; (3) no ground plate is required for the bipolar blade; (4) both monopolar and bipolar blades become fouled with burned tissue fairly quickly; however, operating at lower power settings, the deposit which forms on bipolar blades can be wiped off easily without excessive scrubbing; and (5) when desired, general or spot electro-coagulation of the tissue between the electrodes is readily accomplished.

Thus it is seen that the bipolar blade produces far less burning of the adjacent tissue as the cut is made, while experiencing less drag force.

The center electrode of the bipolar blade is considerably more active than the side electrodes, and thus cutting power is concentrated where it is needed.

The foregoing advantages of this invention will be more readily apparent and appreciated as the same becomes better understood from the following detailed description of the preferred embodiment of the invention when taken in conjunction with the accompanying drawings in which:

BRIEF DESCRIPTION OF THE DRAWINGS

FIG. 4 is a schematic diagram of an enlarged partial side view of the blade and circuitry connected to the blade;

FIG. 5 is a partial enlarged plan view of the split electrode blade;

FIG. 5A is a front end elevational view of the blade of FIG. 5 taken along line 5A'—5A';

FIG. 5B is a rear end elevational view of the blade of FIG. 5 taken along line 5B'—5B';

FIG. 6 is a side elevational view of the split electrode blade of FIG. 5;

FIG. 7 is a perspective view of the unfinished extruded blade body;

DETAILED DESCRIPTION OF THE DRAWINGS

Figure 1:
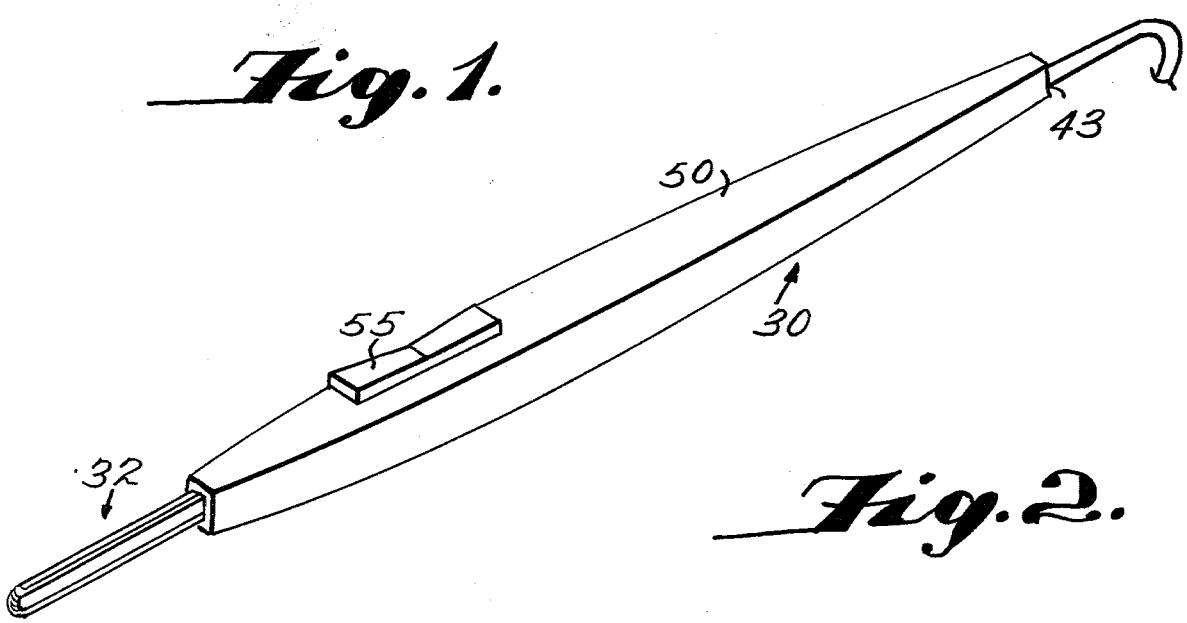
FIG. 1 is a perspective view of the electrosurgical instrument.
Figure 2:
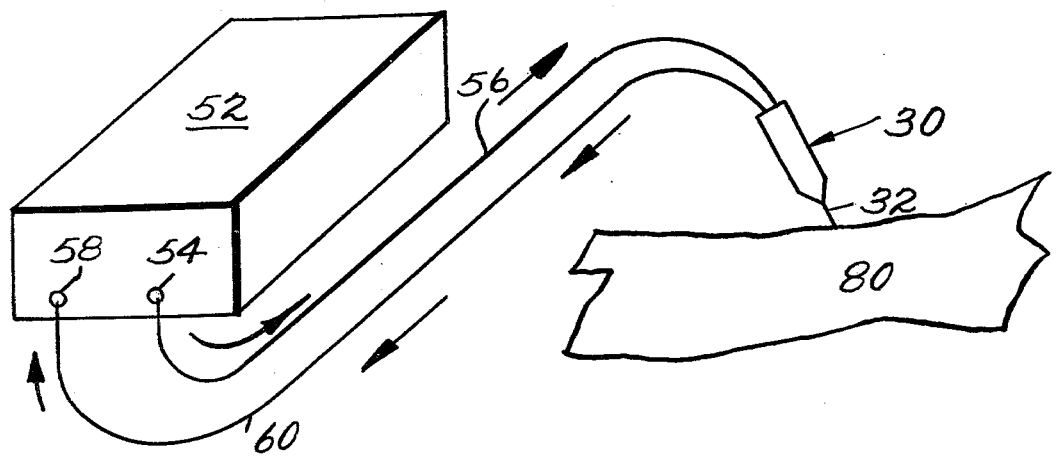
FIG. 2 is a schematic view of the instrument shown in FIG. 1 connected with an electrical wave form generator.

A cutting and coagulating electrosurgical instrument 30 is shown in FIG. 1, In the preferred embodiment of the invention as shown in FIGS. 4–6, the bipolar blade assembly 32 comprises an insulation member 34, a center electrode 36 mounted in the insulation member and split electrodes 38 and 40 secured to insulation member 34. The distal end 33 of the blade assembly is mounted in a blade seat formed in the non-conducting handle casing 50.

Figure 3:
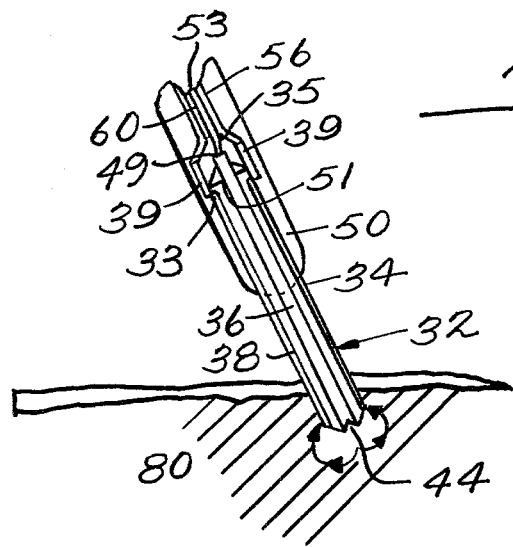
FIG. 3 is an enlarged side schematic view partially in section of the tip of the instrument in FIG. 2 illustrating the currents passing from one conductor to the other through the tissue.

As shown in FIG. 3, the handle casing 50 is provided with contacts 39 which are secured to the casing and positioned adjacent the blade seat 51 which facilitate the electrical connection of the blade electrodes 36, 38, and 40 to the electrosurgical generator 52. As shown in FIG. 4 the split side electrodes 38 and 40 are shorted together within the handpiece and act as electrical return electrodes during the cutting operation. Flexible insulated wires sufficient in length to allow the surgeon unrestricted movement are run through a bore 53 cut through the casing to provide the electrical connection between the contacts and the electrosurgical generator.

The handle 50 is preferably pencil shaped so that it fits the contours of the hand and is shown with a three-way; off, cut and coagulate selector switch 55. The three-way selector switch allows the operator to select the desired mode of wave form emanating from the electrosurgical generator 52. In this manner, the instrument can be used for solely cutting or coagulating. The center electrode member 36 is connected to an active isolated output 54 of the electrosurgical generator 52 through its associated contact and insulated connector wire 56 and split side electrodes 38 and 40 are connected to a patient output 58, which is electrically isolated from ground of the electrosurgical generator 52 through its associated contact and insulated connector wire 60.

Figure 13:
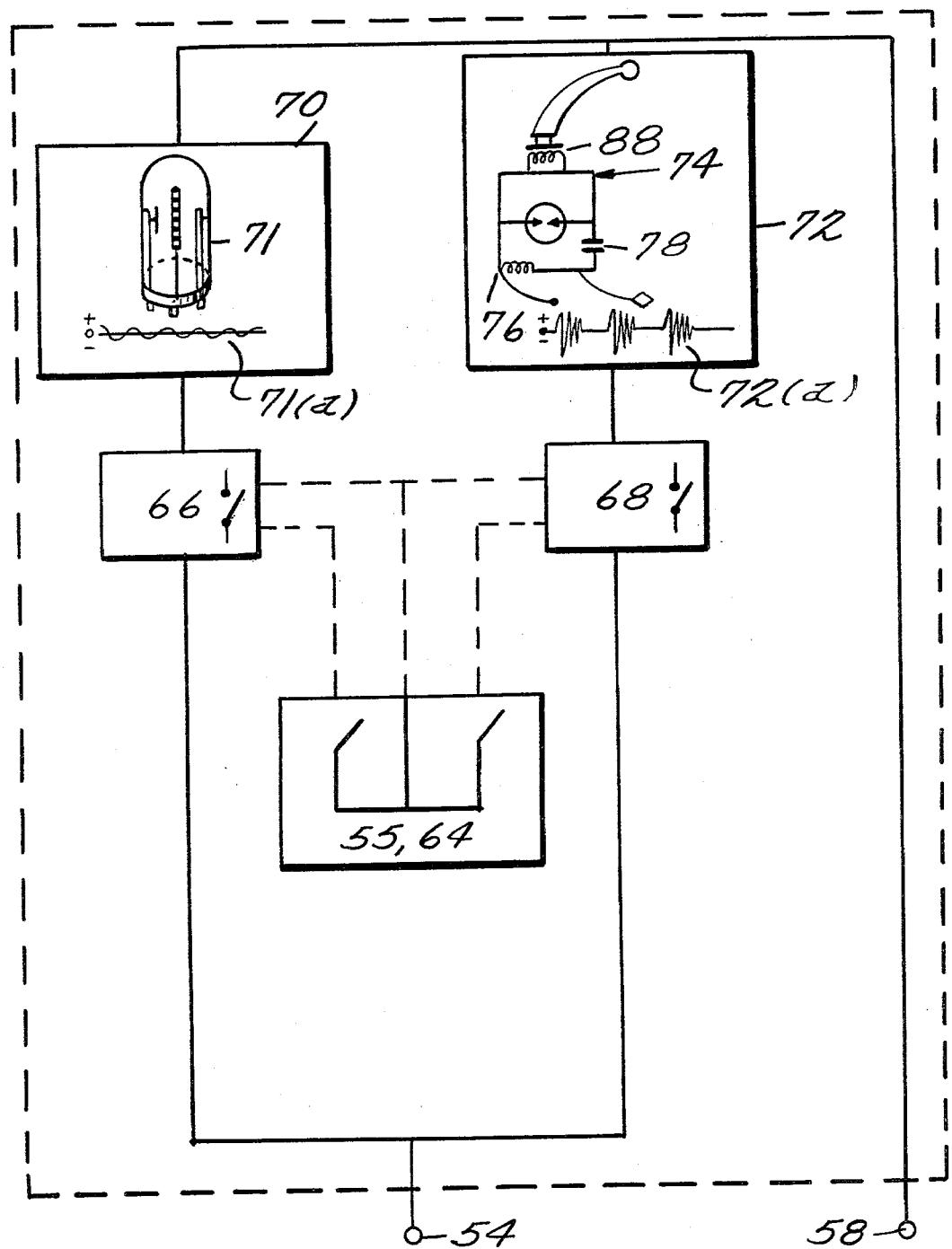
FIG. 13 is an electrical schematic of the electrosurgical generator and switching circuitry.

FIG. 13 of the invention discloses a hand switch 55 or a foot switch 64 selectively connected to power switching devices 66 and 68 so that radio frequency electrical energy for cutting or coagulating wave forms can be passed into output 54 of the electrosurgical generator. Power switching device 66 when activated by the hand switch 55 serves to complete the circuitry schematically shown as block 70. This circuitry 70 is well known in the art to generate cutting forms and is schematically represented by a triode tube 71. Another power switching device 68 is adapted to complete the circuitry schematically shown by block 72 to generate coagulation wave forms which are also well known in the art. Other circuitry and wave forms known in the art can be used in the invention. The spark gap oscillating high frequency circuit 74 has a coil 76 comprising a spiral winding of wire which responds to an alternating current by self-induction to raise the voltage and proportionately lower the amount of current flowing. In the circuit a condenser 78 stores and releases electrical energy and a transformer 88 raises the 110 volt alternating current to about 550 volts. The transformer also isolates the apparatus from the direct power of the current.

In regard to the various types of wave forms generated, this application specifically incorporates the use of commercially available wave form generators such as those manufactured by the Valleylab Inc., Electro Medical Systems, Inc., and Aspen Labs Inc. Two such generators are the EMS System 1101 and the Valley Labs SSE2-K.

Cutting of the tissue by high frequency electrical energy is accomplished with the patient incorporated into the (biterminal) circuit. Cutting occurs through the use of a sine wave 71(a) which is a regular, even, pulsating flow of current. The sine wave causes cellular disruption due to the mechanical forces of the oscillating electrical field with minimal side heat effects. In electrical coagulation, destruction of the tissue is accomplished primarily by heat and secondarily by mechanical forces of the high frequency electrical field. The patient is incorporated into the (biterminal) circuit and the effect is produced by a damped (aperiodic) wave form 72(a). The tissue is cooked or boiled resulting in a complete loss of cellular structure. The sine wave effect is limited almost completely to mechanical disruption of the cells while the damped wave produces both disruption and heat.

Either of the respective wave forms or a combined wave form can be generated through output 54 into the electrosurgical instrument blade. As previously indicated such circuits are well known in the art and are described in previous patents mentioned in the prior art in this invention.

The cutting and coagulation circuitry is shown in FIG. 5B. In FIG. 5B; (A), (B) denote electrode connection to an electrosurgical generator during cutting. The disignation [A], [B] denote electrode connection to an electrosurgical generator during coagulation.

The construction of the blade of the present invention allows for the emission and collection of radio frequency electrical energy in a proximal area causing either cutting or coagulating action depending on the wave form used when the radio frequency electrical energy bridges the gap across the conductors through the tissue 80. When the electrosurgical instrument is activated by switch 55, current passes from output 54 through connection wire 56 in either the cutting or coagulating wave form mode to conductor center electrode 36 and passes through the skin or the tissue 80 of the patient to split side electrode conductors 38 and 40 thereby completing the circuit.

FIGS. 4-7 show the preferred best mode geometrical configuration of the electrosurgical blade. The blade assembly 32 is of a symmetrical construction with the center electrode 36 being mounted in grooves 43 formed in insulation member 34. The insulation member 34 is perferably of a one piece extruded construction. On each side of the insulator member 34 are symmetrical metallized side split electrodes 38 and 40 which are separated from each other by a groove 42 cut in the insulation member 34. Alternatively the groove 42 may be formed by the sides of the split electrodes and the insulation member surface.

Each side of the insulation member 34 is comprised of a planar center section 35 and angled side sections 37. The sides of the insulation member 34 are separated by a groove 43 cut into the periphery of the insulation member to hold the center electrode 36. The grooves 43 are preferably angularly cut into the insulator member so that the base 45 is wider than the entrance 41. This increased width allows the bonding material to be placed in the base and gather along the groove walls when the center electrode 36 is mounted into the grooves 43. Each side of the insulation member comprises a front end 46 formed with a front center section 47 angled rearward and two beveled side sections 48 angled towards the rear of the blade at an approximate 45° angle from the front center section. Metallized ends 50 of the side split electrode 38 and 40 are mounted to the front center section 47 and terminate at a plane defined by grooves 43. The split side electrodes 38 and 40 and their respective end portions 50 form a continuous path around each side of the insulation member and form an elongated "L" shape on the insulation member 34.

The groove or space 42 runs longitudinally along the insulation member and is preferably cut into the surface of the insulation member from 0.005 inches to 0.01 inches in depth and from 0.01 to 0.03 inches in width. The tolerances of depth and width are ±0.003 inches and the tolerances in radius are ±0.003 inches. The radius for the purpose of the application are the corners of the groove 42. The blade insulation member in the best mode is preferably extruded and approximately 0.160 inches wide ±0.003 inches, and 1.500 inches long ±0.005 inches with a groove 0.027 inches wide ±0.005 inches cut into it and a tab portion 0.530 inches long ±0.015 inches. The groove 42 forms a barrier which prevents arcing from one split electrode to the other split electrode. Optimally each split electrode and end section is 0.015 to 0.019 inches in width and is placed near the edge of the insulation member leaving a 0.001 to 0.0 inches distance between the side of the electrode and the edge of the insulation member. The center electrode which is 0.010 inches thick ±0.001 inches is mounted in side grooves 43 cut into the sides of the insulation member and extends in the preferred embodiment beyond the insulation member 0.010 to 0.015 inches so that the ratio of return electrode area to active electrode area ranges from about 0.70 to 2.0.

The formula R = return electrode area/active electrode area allows the electrode ratio to be determined. The optimum operating ratio of the invention which has presently been found by experimentation lies between the 1.1–1.5 range.

The center electrode 36 can have beveled edges 102 and 104 which form an angular cutting surface around the electrode body. A recessed "V" shaped tip 44 is cut in the front end of the center electrode as shown in FIG. 3 while the end 49 of the center electrode forms flat planar surfaces for center electrode contact tab 35.

When the blade is inserted into the handle 50, the center electrode contact tab 35 is fitted into the blade seat of the instrument and is connected directly to insulated connector wire 56.

Figure 11:
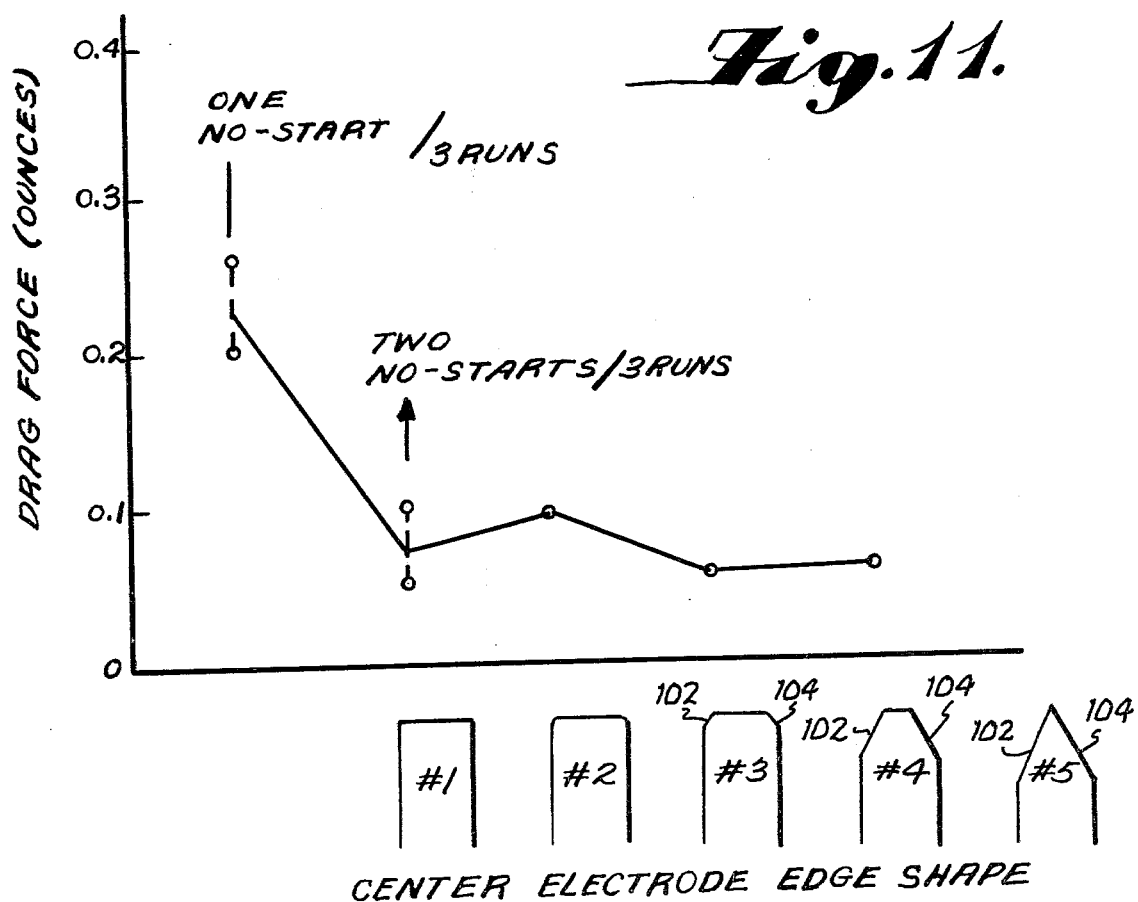
FIG. 11 is a graph charting cutting drag force in relation to the center electrode edge shape used in the blade assembly.

The insulator member 34 is preferably constructed in a one piece extruded form and evidences a trapazoidal configuration when viewed from the top. Insulation member 34 is comprised of two flat surfaces 112 and 114 forming a top and bottom in which grooves 42 are cut, adjacent to which the split side electrodes 38 and 40 are mounted. Angled flat surfaces 116 and 118 extend towards each other and are intersected by surfaces 112 and 114. The angled or beveled surfaces 116 and 118 are separated by a groove 43 which holds the center electrode 36. Alternate beveled, side edges 102 and 104 of the center electrode as shown in FIG. 11 extend beyond the beveled sides 116 and 118 of the insulation member to provide a cutting edge around the blade. A vertical rear wall 122 and beveled front end 46 of the insulator member form the boundaries of the member as shown in FIG. 5. The front end 46 is formed with beveled side surfaces 48 to form a cutting edge.

In the preferred embodiment the angle formed by the adjacent beveled surfaces 116 and 118 of the insulation member 34 and the center electrode 36 is about 60°. This angle $\theta_W$ formed between the adjacent beveled side of walls 116 and 118 of the insulator member and center electrode, will be later discussed. The angle is constant along the side walls of the insultion member and the center electrode 36. As previously indicated, the center electrode 36 can also define two beveled surfaces 102 and 104 which form the same critical angle.

The side or outer split electrodes 38 and 40 are thin sheets of a metallized substance such as silver which is silk screen applied to the insulation member before firing. The insulation member 34 alternatively can be constructed of two identical members which are bonded together by high temperature commercially available epoxy.

The split electrode blade design, shown schematically in FIG. 4 is a practical solution to the "starting" problem occurring when the blade is first used to provide an initial incision. The split electrode design substantially eliminates the high drag force occurring at the beginning of a cut by limiting the area of the center electrode in contact with the body tissue. Due to the fact that the AC output of the power supply is fully isolated, the electrode making best contact with the tissue remains nearly at the potential of the tissue, and is thus inactive. The limited area of the center electrode results in its being active continuously, consequently allowing successful starts. As also indicated in FIG. 4, the side electrodes 38 and 40, which tend to be inactive, are shorted together within the handpiece and act as the return electrode during cutting. The bipolar blade, when compared to the monopolar blade produces less burning of the adjacent tissue as the cut is made and experiences less drag force. The drag force is the amount of opposing force a portion of body tissue will exhibit to cutting with a specific bi-polar or monopolar electrosurgical blade.

Figure 9:
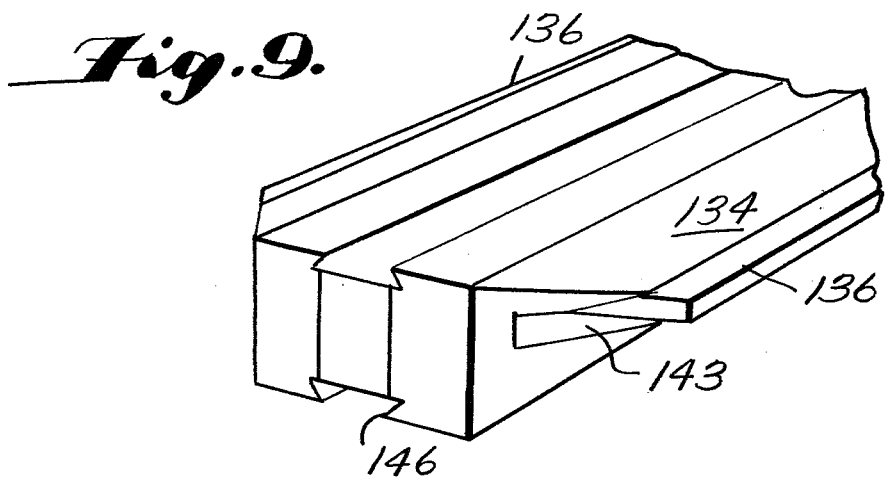
FIG. 9 is an enlarged partial front end view of the alternate embodiment blade shown in FIG. 8.
Figure 8:
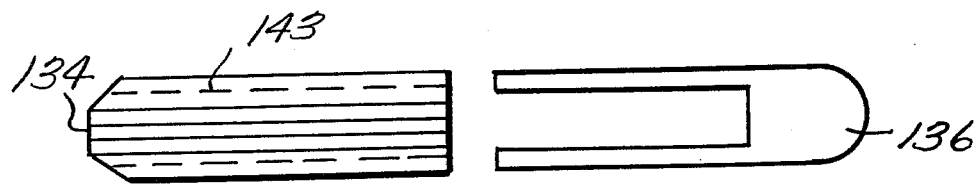
FIG. 8 is an exploded plan view of an alternate embodiment of the split electrode blade.

FIGS. 8 & 9 disclose an alternate embodiment of the invention. In this alternate embodiment the entire tip is metallized.

The active blade 136 has the appearance of a "tuning fork" as is best shown in FIG. 8. The stainless steel active electrode 136 is pushed along slots 143 cut into the insulation member 134 until it rests adjacent the front end 146 of the insulation member as shown in FIG. 9.

Figure 10:
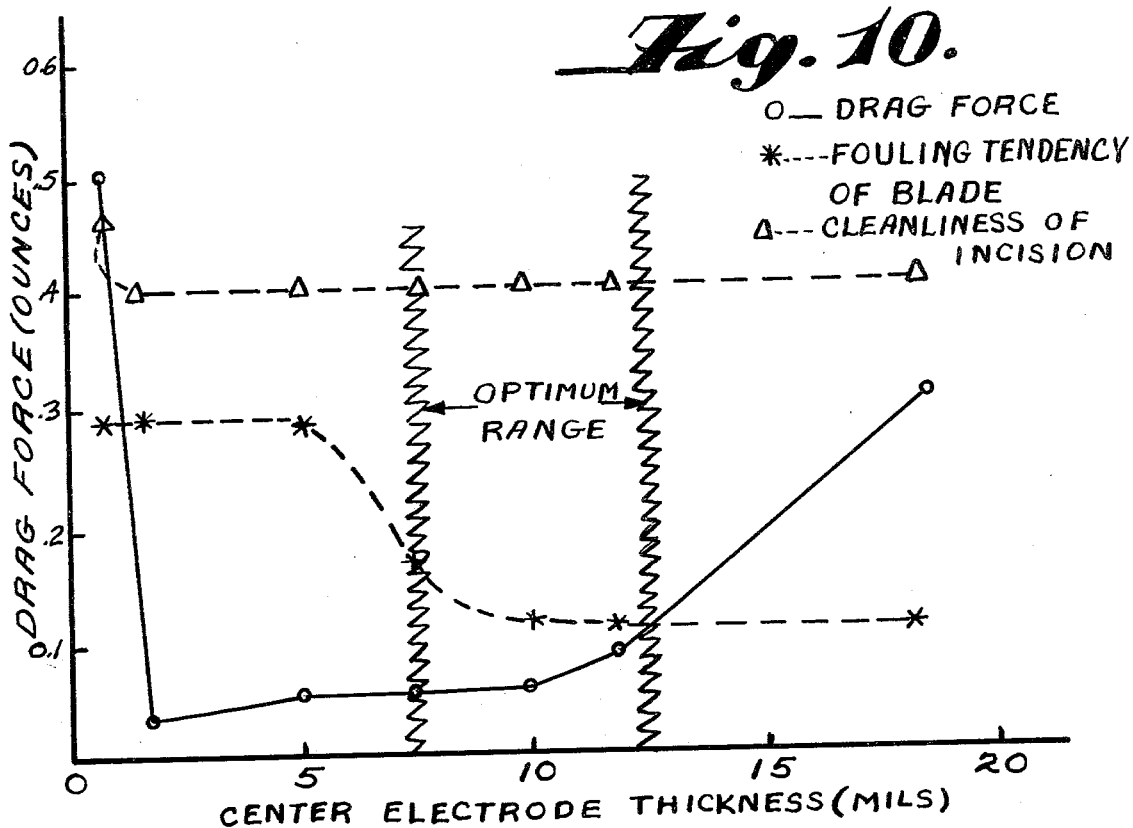
FIG. 10 is a graph charting cutting drag force, cleanliness of cut and fouling tendency in relation to the thickness of center electrode used in the blade assembly.

FIG. 10 is a graph illustrating the increase in drag force and blade fouling as a function of the thickness of the center electrode for a 316 L stainless steel center electrode. It can be seen that optimum results are obtained when the thickness of the center electrode is in the range of 0.0075 to 0.013 inches. The preferred embodiment contemplates the center electrode thickness as 0.010 inches in thickness extending beyond the insulated member 0.010 inches. The end members 50 are 0.018 inches in width and extend down the insulation member face 0.028 inches with their inner edges spaced apart 0.027 inches. The split side electrodes are preferably 0.018 inches in width separated by a groove 42 0.027 inches in width. The beveled side sections 48 are cut at an approximate 45° angle with respect to the center front section. The notch is cut into the insulation member 24 approximately 0.058 inches from the front surface so that a ratio from 1.1 to 1.2 is formed. This has been determined as the best compromise between cutting drag force and the blade fouling. Other center electrode materials may be used such as tantalum.

FIG. 11 is a graphical illustration of the center electrode edge shape and resultant drag force determined by the center electrode edge shape. The corners of the blade tips were beveled in varying amounts as indicated in FIG. 11 with beveling tips shown in numbers 3–5 performing with only minor differences in drag force. Numbers 1 and 2 had significant starting difficulty on several runs due to the edge shape.

Figure 12:
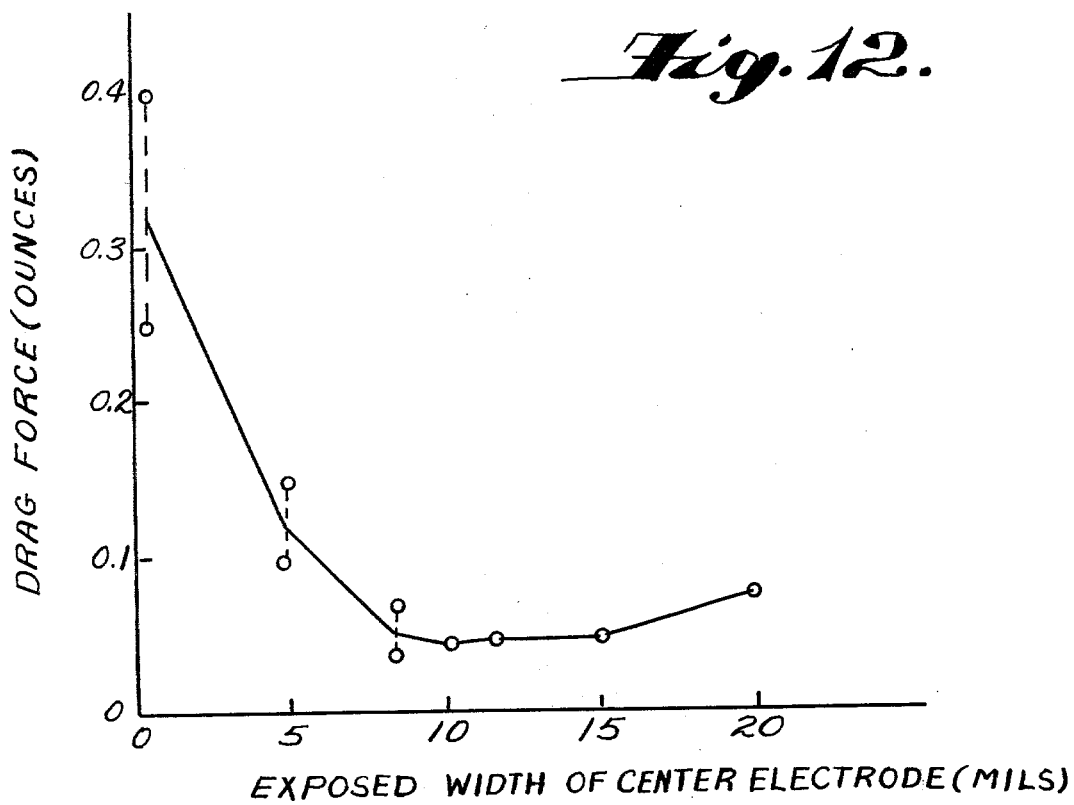
FIG. 12 is a graph charting cutting drag, in relation to the exposed width of the center electrode of the blade assembly.

FIG. 12 is a graphical illustration of the drag force (measured in ounces) as a function of the exposed width (in inches) of the center electrode. As can be readily seen, exposed widths of from 0.008 to 0.02 inches offer good performance with the optimum width being in the range of 0.01 inches to 0.015 inches.

Experience with manual cutting has shown that the RF potential supplied to blades is an important variable in the behavior of the blades, and that monopolar and bi-polar blades respond differently to changes in power.

Inherent in the split electrode design is a relatively high current density located at the center electrode. Center electrodes composed of a highly refractory metal perform adequately and the material for the center conductor must be both reasonably refractory and medically acceptable. Requirements for the materials used in the side electrodes are far less stringent.

A substantial amount of tissue toxicity work has been done in neural tissue, since it is quite delicate and represents a "worst case" model. Orthopedic appliance research has also been responsible for much of the information available on the toxicity of implanted materials. Research in this area involves both hard and soft tissues, especially bone, tendon, cartilage and muscle. A great deal of work has been performed involving endiothelial cultures because of the necessity for a material which can provide variable feed-through between the physiological and the external environment.

These studies indicate that certain materials are toxic to animal tissue while other materials are non-toxic and therefore medically acceptable. Materials selected from those non-toxic materials can be used for the center electrode for bi-polar cutting blades if the required physical material requirements are met. Another consideration in the choice of materials is the fact that the tissue immediately adjacent to the incision made with an electrosurgery blade is destroyed. Thus, this tissue may be replaced by non-functional scar tissue. The effects of small amounts of metal or ceramic in fibrous scar tissue should be negligable. Non-toxic materials, which have been considered in the present invention and are medically acceptable for the present electrosurgical application, include tantalum, molybdenum, nickel, aluminum, nichrome, selected stainless steels such as 316 stainless steel, iridium, $Al_2O_3$, Steatite, Forsterite, Zircon, and selected glasses.

In the preferred embodiment either tantalum or stainless steel are employed as the material composition for the center electrode. Early bi-polar design experienced a great deal of difficulty with destructive areas, and it was found that high purity $Al_2O_3$ was necessary to avoid catastrophic breakdowns. In the preferred embodiment of the blade the insulator member 34 is comprised of $Al_2O_3$, 96–99 plus percent pure. While $Al_2O_3$ is the preferred insulator material, certain material characteristics have been found which result in alternative acceptable bi-polar blade insulators. These characteristics are (1) a maximum loss factor of 0.003 (@25° C. and 1 $MH_z$), (2) a minimum dielectric strength of 200 volts/-mil (@25° C. and 60 $MH_z$), and (3) a minimal flexible strength of 50,000 (p.s.i). Acceptable insulator material coming within these criteria are $Al_2O_3$ material manufactured by 3 M Company designated #772 and 805; Coors AD-995, Duramic HT-990 and HT-998. Other potential side electrode materials are Mo-Mn composition. These metallizers, while having a lower cost and adhering better to ceramics, require a silver or gold plating over them in order to shield them from the body tissue during cutting or cauterizing. The preferred embodiment utilizes metallized silver of a silver 6216 composition manufactured by Dupont as the composition of the side split elelectrodes. The side electrodes operate at a much lower potential than the center electrode and so may be of a less refractory metal that is relatively easy to apply. Since insignificant amounts of the side electrodes will be deposited along the incision, a material such as silver, while not suitable for implants because of its long term corrosion behavior, does not present a histological problem.

A method of assembly of the blades, i.e. bonding the insulation half member onto the center electrode with commercially available Ecco Bond 104, cured at 400° F., provides a dramatic increase in bending strength. Differential thermal contraction of the metal center electrode during cooling results in a residual compressive stress in the $Al_2O_3$ side members, a condition analogous to that found in pre-stressed concrete beams.

While the preferred embodiment of the invention has been disclosed, it is understood that the invention is not limited to such an embodiment since it may be otherwise embodied in the scope of the appended claims.

What is claimed is:

1. An electrosurgical instrument of the type adapted to be selectively connected to a source of energy such as a high frequency electrical current for use in cutting, coagulating or otherwise treating human tissue or the like comprising an insulative handle and blade assembly mounted in said handle and extending therefrom, said blade assembly comprising an insulation member having an alumina composition of at least 96% purity, a linearly shaped active center electrode mounted to said insulation member, a plurality of return electrodes symmetrically mounted to said insulation member spaced apart from said center electrode and each other, a portion of said center electrode extending beyond said insulation member, said center electrode portion and sides of said insulation member forming a blade assembly having a beveled edge, means for connecting said electrodes to an energy source means so that an output circuit of a source of energy comprising a high frequency electrical current is completed through body tissue, said energy source means comprising means to selectively generate and conduct wave forms to said electrodes for performance of the desired electrical function.

2. A surgical instrument as claimed in claim 1 wherein said center electrode is stainless steel.

3. A bipolar electrosurgical device adapted for connection to a high frequency electrical generator having active and return output terminals, said device being used to cut, coagulate, or otherwise treat human tissue or the like, said device comprising a high purity composition of about 96% alumina insulative electrode support means defining a beveled surface; an active electrically conductive electrode responsive to said active output terminal and return electrodes comprising conductive elements responsive to said return output terminal, said electrodes being supported by said electrode support means, said return electrodes being symmetrically disposed with respect to said active electrode with the active electrode positioned intermediate the return electrodes, said active and return electrodes being rigidly supported a fixed distance apart by said electrode support means, said electrodes being adapted for electrical connection to said tissue, the ratio of the return electrode area adapted to electrically connect to said tissue as compared to the active electrode area adapted to electrically connect to said tissue being in the range of approximately 0.70 to 2.0, and means for connecting said active electrode to said active output terminal and said return electrodes to said return output terminal so that said electrosurgical device can be used to treat said tissue.

4. An electrosurgical device as claimed in claim 3 wherein said ratio has a preferred range of 1.1–1.5.

5. An electrosurgical device as claimed in claim 3 wherein said return electrodes comprise a plurality of spaced apart parallel conductive elements at least 0.015 inches in width positioned on said electrode support means, said electrode support means defining a groove which is located between said spaced conductive elements separating said spaced conductive elements.

6. A bipolar electrosurgical device as claimed in claim 5 wherein said plurality of conductive elements include end sections forming an "L" shaped configuration.

7. An electrosurgical device as claimed in claim 3 wherein said active electrode element is shaped like a tuning fork and mounted around said insulative electrode support means.

8. An electrosurgical device as claimed in claim 7 wherein said active electrode element has its forward cutting edges beveled inward.

9. An electrosurgical device as claimed in claim 3 wherein said insulative electrode support means can withstand a stress of 50,000 p.s.i. and has a dielectric strength greater than 200 volts/mil at 25° C. and 60 $MH_z$.

10. An electrosurgical instrument adapted for connection of a high frequency electrical generator having active and return output terminals, said instrument being used to cut, coagulate or treat animal tissue and comprising an insulated handle and blade assembly mounted in said handle and extending from said handle, said blade assembly comprising a linearly formed insulation member, an active electrode mounted to said insulation member and extending from at least two sides of said insulation member 0.0075 to 0.02 inches, said insulation member having an $Al_2O_3$ composition ranging from 96 to 99% plus purity, a plurality of spaced outer return electrodes secured to said insulation member and symmetrically positioned on said insulation member, the ratio of the area of said return electrodes to the area of said active electrode ranging from 1.1–2.0, means for connecting said electrodes to said generator so that an output circuit comprising a high frequency electrical current is completed through tissue intervening between and in contact with said electrodes, said generator comprising means to generate cutting or coagulating wave forms to said electrodes and switch means adapted to selectively transmit said wave forms into said electrodes for performance of the desired electrosurgical function.

11. A surgical instrument as claimed in claim 10 wherein said outer return electrodes are a nobel metal combination about 0.015 to 0.018 inches in width and are positioned parallel to each other.

12. A blade assembly suitable for use with a bipolar electrosurgical instrument comprising a linearly shaped active center electrode ranging from 0.0075 to 0.015 inches in thickness and having a substantially "U" shaped configuration, an alumina insulation member of at least 96% purity defining a plurality of grooves, said electrode being mounted in said grooves formed in said alumina insulation member and extending from said alumina insulation member to form a blade edge, a plurality of spaced apart symmetrical side return electrodes secured to opposite sides of said insulation member to form a ratio R with respect to the active center electrode defined by:

$$R = \text{Return electrode area/Active electrode area}$$

with R ranging in value from 1.2–1.8, said center electrode and insulation member forming a blade edge.

13. A blade assembly as claimed in claim 12 wherein said insulation member has a material composition of $Al_2O_3$ 99.5% plus purity.

14. An electrosurgical instrument comprising an insulative handle, a blade assembly mounted in said handle and extending therefrom, said blade assembly comprising an alumina insulation structure of at least 96% purity having a dielectric strength greater than 200 volts/mil at 25° C. and 60 MHz and withstanding a compressive stress of at least 50,000 p.s.i., a linearly shaped active center electrode mounted to and extending from said insulation structure, a plurality of return electrodes symmetrically mounted to said insulation structure spaced apart from said center electrode and each other, said center electrode and insulation structure forming a blade assembly having a beveled edge with the center electrode and return electrodes extending near the tip of the blade assembly and the return electrodes being located proximate to the beveled edge of the insulation structure and means for connecting said electrodes to an energy source means so that an output circuit of a source of energy comprising a high frequency electrical circuit is completed through body tissue.

15. A bipolar electrosurgical device adapted for connection to a high frequency electrical generator having active and return output terminals, said device being used to cut, coagulate, or otherwise treat human tissue or the like, said device comprising an insulative electrode support means of at least 96% purity alumina defining a tip with a front section and beveled sides, said tip being beveled at an approximately 45° angle with respect to the front section; an active electrode formed with an outer edge having a thickness not greater than 15 mils responsive to said active output terminal and return electrodes comprising conductive elements responsive to said return output terminal, said electrodes being supported by said electrode support means, said return electrodes being symmetrically disposed with respect to said active electrode with the active electrode positioned intermediate the return electrodes, said active and return electrodes being rigidly supported a fixed distance apart by said electrode support means, said electrodes being adapted for electrical connection to said tissue, the ratio of the return electrode area adapted to electrically connect to said tissue as compared to the active electrode area adapted to electrically connect to said tissue being in the range of approximately 0.70 to 2.0, and means for connecting said active electrode to said active output terminal and said return electrodes to said return output terminal so that said electrosurgical device can be used to treat said tissue.

16. A blade assembly suitable for use with a bipolar electrosurgical instrument comprising a linearly shaped active center electrode body, said electrode body being mounted in a beveled alumina insulation member of at least 96% purity, said electrode body having an exposed width ranging from 0.008 to 0.02 inches, a plurality of spaced apart split symmetrical side return electrodes secured to opposite sides of said insulation member to form a ratio R with the active electrode defined by:

$$R = \text{Return electrode area/Active electrode area}$$

with R ranging in value from 0.7–2.0, said center electrode body being beveled and mounted to said insulation member to form a cutting blade edge, and said return electrodes and said insulation member forming a coagulation blade edge.

17. A blade assembly as claimed in claim 16 wherein said beveled alumina insulation member and said beveled center electrode body form an angle of about 60° to define the cutting blade edge.

18. A blade assembly suitable for use with a bipolar electrosurgical instrument comprising a linearly shaped active center electrode body ranging from 0.0075 to 0.015 inches in thickness mounted to an alumina insulation member of at least 96% purity, said insulation member defining beveled side portions forming an angle of about 60° and an angled front section, a plurality of spaced apart symmetrical side return electrodes secured to opposite sides of said insulation member forming an area ratio R with respect to the active center electrode which is defined by:

$$R = \text{Return electrode area/Active electrode area}$$

with R ranging in value from 0.70–2.0, said center electrode and the beveled side portions of said insulation member forming a blade edge for cutting and said side return electrodes forming a coagulation edge.

19. A bipolar electrosurgical instrument for cutting animal tissue comprising an insulative handle and blade assembly mounted in and extending from said handle, said blade assembly comprising a beveled insulation member having an Al$_2$O$_3$ composition of greater than 96% purity, a linearly shaped active center electrode ranging from 0.005 to 0.015 inches in thickness mounted to said insulation member and extending beyond said insulation member, a plurality of return electrodes symmetrically mounted to said insulation member spaced apart from said center electrode and each other, said center electrode and insulation member forming a blade assembly with the proximity of the return electrodes to the bevel allowing shallow cutting when the tissue is under tension, means for connecting said electrodes to an energy source means so that an output circuit of a source of energy comprising a high frequency electrical circuit is completed through body tissue.

* * * * *

UNITED STATES PATENT OFFICE
CERTIFICATE OF CORRECTION

Patent No. 4,202,337  Dated May 13, 1980

Inventor(s) John J. Hren et al.

It is certified that error appears in the above-identified patent and that said Letters Patent are hereby corrected as shown below:

[75] Inventors: John J. Hren; David E. Clark; David A. Jenkins; Paul F. Johnson, III, all of Gainesville; Howard E. Degler, Jr.; St. Petersburg, all of Florida.

Signed and Sealed this

Tenth Day of February 1981

[SEAL]

Attest:

RENE D. TEGTMEYER

Attesting Officer    Acting Commissioner of Patents and Trademarks